US010650455B2

(12) United States Patent
Madle et al.

(10) Patent No.: US 10,650,455 B2
(45) Date of Patent: *May 12, 2020

(54) METHODS, SOFTWARE, AND SYSTEMS FOR OVER-THE-COUNTER TRADING

(71) Applicant: Intercontinental Exchange Holdings, Inc., Atlanta, GA (US)

(72) Inventors: Stephen Richard Madle, London (GB); Forbes Herbert Elworthy, London (GB)

(73) Assignee: Intercontinental Exchange Holdings, Inc., Atlanta, GA (US)

( * ) Notice: Subject to any disclaimer, the term of this patent is extended or adjusted under 35 U.S.C. 154(b) by 54 days.

This patent is subject to a terminal disclaimer.

(21) Appl. No.: 15/192,955

(22) Filed: Jun. 24, 2016

(65) Prior Publication Data

US 2017/0148094 A1 May 25, 2017

Related U.S. Application Data

(63) Continuation of application No. 13/523,342, filed on Jun. 14, 2012, now abandoned, which is a (Continued)

(51) Int. Cl.
*G06Q 40/04* (2012.01)
*G06Q 20/10* (2012.01)
(Continued)

(52) U.S. Cl.
CPC ........... *G06Q 40/04* (2013.01); *G06Q 20/10* (2013.01); *G06Q 20/382* (2013.01); *G06Q 40/06* (2013.01); *G06Q 50/24* (2013.01)

(58) Field of Classification Search
CPC .............................. G06Q 40/04; G06Q 20/382
(Continued)

(56) References Cited

U.S. PATENT DOCUMENTS 4,674,044 A * 6/1987 Kalmus .............. G06Q 40/04
340/4.5
5,297,032 A 3/1994 Trojan et al.
(Continued)

FOREIGN PATENT DOCUMENTS

WO 9918821 A1 4/1999
WO 9919821 A1 4/1999

OTHER PUBLICATIONS

"GlobeOp Enhances Platform With Markit's Credit Data," Globe Newswire, Jul. 7, 2005. (http://globenewswire.com/news-release/2005/07/07/329875/81376/en/GlobeOp-Enhances-Platform-With-Markit-s-Credit-Data.html).

*Primary Examiner* — Robert R Niquette
(74) *Attorney, Agent, or Firm* — DLA Piper LLP (US)

(57) ABSTRACT

Methods, software, and hardware are disclosed for providing verified real time price quotes in an over-the-counter financial market. Systems are described that can comprise methods, software, and/or hardware to provide verified real time price information for securities traded over-the-counter. Verification methods of the invention include identifying suspect source data, wherein the suspect source data includes information about the price of a security, verifying the suspect source data, and displaying to a user a verified price quote of a security traded in an over-the-counter market to a user. The verification methods of the invention include using hash functions and hash tables to process suspect source data, wherein the hashing allows for confidential processing while at the same time maintaining the ability to match a price quote to the source of the price quote.

22 Claims, 11 Drawing Sheets

Related U.S. Application Data continuation of application No. 11/216,490, filed on Aug. 31, 2005, now Pat. No. 8,224,738.

(51) Int. Cl.
  *G06Q 40/06* (2012.01)
  *G06Q 20/38* (2012.01)
  *G06Q 50/24* (2012.01)

(58) Field of Classification Search
  USPC .......................................................... 705/37
  See application file for complete search history.

(56) References Cited

U.S. PATENT DOCUMENTS

| | | |
|---|---|---|
| 6,272,474 B1 | 8/2001 | Garcia |
| 6,347,307 B1 | 2/2002 | Sandhu et al. |
| 6,408,282 B1 | 6/2002 | Buist |
| 6,617,969 B2 | 9/2003 | Tu et al. |
| 6,697,810 B2 | 2/2004 | Kumar et al. |
| 7,116,782 B2 | 10/2006 | Jackson et al. |
| 2002/0007452 A1 | 1/2002 | Traw et al. |
| 2002/0154010 A1 | 10/2002 | Tu et al. |
| 2002/0156601 A1* | 10/2002 | Tu ........................ G06Q 10/10 702/188 |
| 2002/0156785 A1 | 10/2002 | Kumar et al. |
| 2002/0157017 A1 | 10/2002 | Mi et al. |
| 2002/0161693 A1 | 10/2002 | Greenwald |
| 2002/0188548 A1 | 12/2002 | Bunda |
| 2003/0009411 A1 | 1/2003 | Ram et al. |
| 2003/0033212 A1 | 2/2003 | Sandhu et al. |
| 2003/0131240 A1 | 7/2003 | Greene et al. |
| 2003/0229716 A1 | 12/2003 | Holland |
| 2005/0114260 A1 | 5/2005 | Gula, IV |
| 2005/0246261 A1* | 11/2005 | Stevens .................. G06Q 40/00 705/37 |
| 2005/0273413 A1* | 12/2005 | Vaudrie .................. G06Q 40/00 705/36 R |
| 2006/0218013 A1 | 9/2006 | Nahra et al. |
| 2007/0005481 A1* | 1/2007 | Kedia .................... G06Q 40/04 705/37 |
| 2007/0005485 A1* | 1/2007 | Tumen ................. G06Q 20/042 705/37 |
| 2008/0140559 A1 | 6/2008 | Ram et al. |
| 2008/0154633 A1 | 6/2008 | Ishibashi et al. |
| 2009/0063351 A1 | 3/2009 | Schmeyer et al. |
| 2010/0198745 A1* | 8/2010 | Davin, III ............. G06Q 40/00 705/36 R |
| 2012/0203682 A1* | 8/2012 | Angle ................... G06Q 40/00 705/37 |

* cited by examiner

METHODS, SOFTWARE, AND SYSTEMS FOR OVER-THE-COUNTER TRADING

RELATED APPLICATION DATA

This application is a continuation of U.S. patent application Ser. No. 13/523,342, filed Jun. 14, 2012, now pending, which is a continuation of U.S. patent application Ser. No. 11/216,490, filed Aug. 31, 2005, now U.S. Pat. No. 8,224, 738, the entire disclosures of each of which are hereby incorporated by reference herein in their entireties.

FIELD OF THE INVENTION

The present invention relates to methods, software, and systems for generating verified price quotes in a financial market, including in an over-the-counter securities market. The invention also relates to methods of identifying suspect data wherein the suspect data comprises a price quote for a security in a financial market. The invention comprises methods, software, and systems for verifying financial information, such as price quotes, from one or more sources, including transmitting suspect data electronically in encrypted form, and displaying verification status of the suspect data. The invention comprises using hash functions in analyzing price quote data in a financial market.

BACKGROUND

Unlike equities, many financial asset classes do not trade on an electronic exchange with real-time price discovery and execution, but instead trade in what is referred to as an "over-the-counter" (OTC)market.

Participants in these over-the-counter markets source pricing levels and execute trades primarily via email, telephone and broker websites. As young markets develop and more assets begin trading, the volume of data received—particularly via email—rapidly becomes too large to be efficiently assimilated. In order for traders to discover the best prices, and with whom they should execute the trade, traders must scour through their email inboxes and numerous websites to find the best quotes.

Every day, traders receive huge volumes of pricing data in heterogeneous formats via different media. Without a system for handling that data, much—if not all of it—is effectively useless. Methods, software, and systems by which traders in certain over-the-counter derivatives can identify, organize and store, in real time, heterogeneous pricing data received via email or the web from dealers, would facilitate more efficient trading. Accordingly, methods, software, and systems for determining best prices and trading partners are needed for efficient trading in over-the-counter markets.

SUMMARY OF INVENTION

Methods, software, and systems are disclosed for providing real-time source data information in over-the-counter financial markets. Various embodiments are disclosed wherein the methods, software, and systems described herein manipulate source data to achieve presentation of pricing information in real time for traders in over-the-counter markets. Presentation of pricing information in real time includes immediate capture and display of structured data captured from structured and unstructured data sources, as opposed to delayed structuring and display of data that would, for example, result from manual data entry.

The invention comprises methods for providing a price quote on a security traded in an over-the-counter financial market, comprising: receiving source data comprising price information of the security; storing the source data on a computer readable medium; processing the source data using a computer processor, wherein the processing comprises extracting a price quote from the source data for the security, comparing the price quote to at least one pre-selected criterion, and storing the compared price quote on a computer readable medium; and, transmitting the compared price quote. The compared price can be transmitted to system users, such as, for example, traders and risk managers, and in the case of exception data, data editors for manual validation.

The methods comprise embodiments wherein the source data is received from multiple sources and wherein the source data comprises more than one price quote for the security.

In various embodiments, the source data received from at least a first source and a second source, wherein the source data received from the first source is in a different format than the source data received from the second source. Various formats of the source data include those comprising an email, html, text, xml, or combinations thereof.

Various embodiments include processing the source data by parsing the source data before comparing the source data to the pre-selected criterion (or criteria). The parsing may comprise categorizing words, patterns, and/or numbers in the data source to identify market data or the price quote in the source data.

Methods of the invention are also provided that comprise designating source data that does not meet the criterion (or criteria) as suspect data.

The invention also comprises methods, software, and systems for generating verified price quotes for securities traded in an over-the-counter financial market, comprising: receiving source data comprising information about the price of a security; storing the source data on a computer readable medium; processing the source data using a computer processor, wherein the processing comprises identifying suspect source data, assigning a hash key to suspect source data, wherein the hash key comprises a price quote and the identity of the data source; verifying the suspect source data using the hash key, and converting the hash key into a verified price quote. In various embodiments, the hash key can be encrypted.

The invention also comprises a method for computing VaR, comprising employing the methods of the invention to generate real time price quotes, including verified price quotes, and using the real time price quotes in a VaR method. Any suitable VaR model or algorithm can be used in connection with the invention. In some embodiments, the invention comprises employing the methods of the invention to generate verified price quotes and using the verified price quotes to compute a VaR for a portfolio, wherein the VaR is employed to set trading limits on the securities comprising the portfolio.

For a better understanding of the present invention together with other and further advantages and embodiments, reference is made to the following description taken in conjunction with the examples, the scope of the which is set forth in the appended claims.

BRIEF DESCRIPTION OF THE FIGURES

The preferred embodiments of the invention have been chosen for purposes of illustration and description but are not intended to restrict the scope of the invention in any way. The preferred embodiments of certain aspects of the invention are shown in the accompanying figure, wherein.

DETAILED DESCRIPTION OF INVENTION

Figure 1:
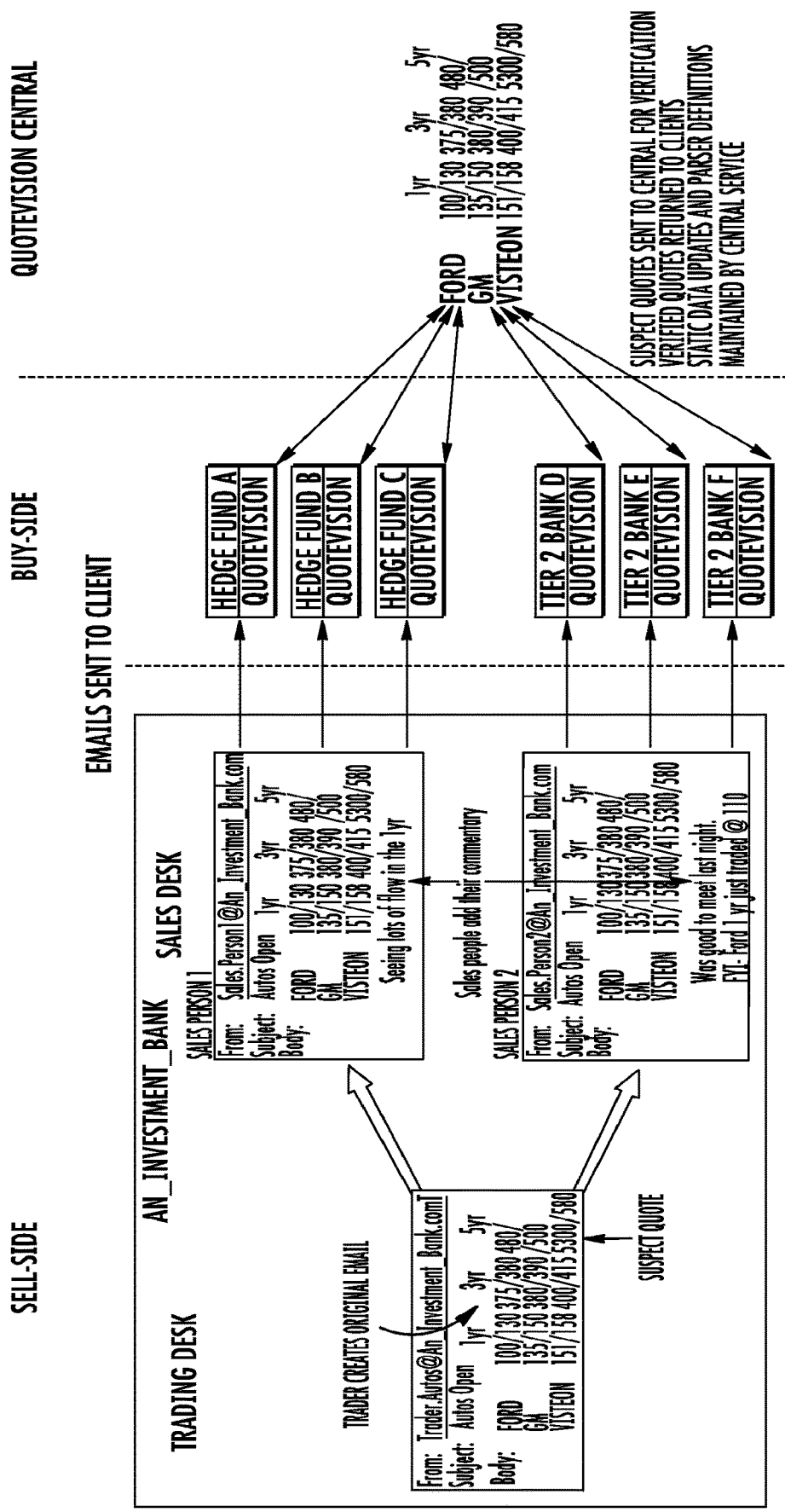
FIG. 1 illustrates market data flow in an investment bank, comprising a verification process for suspect price quotes employing a central database for verifying suspect quotes.

The present invention will now be described in connection with preferred embodiments. These embodiments are presented to aid in an understanding of the present invention and are not intended to, and should not be construed, to limit the invention in any way. All alternatives, modifications and equivalents that may become obvious to those of ordinary skill upon reading the disclosure are included within the spirit and scope of the present invention.

This disclosure is not a primer on computer software or hardware; basic concepts known to those skilled in the art have not been set forth in detail.

One aspect of the present invention comprises a method for providing a price quote on a security traded in an over-the-counter financial market, comprising: (a) receiving source data comprising price information of the security; (b) storing the source data on a computer readable medium; (c) processing the source data using a computer processor, wherein the processing comprises extracting a price quote from the source data, comparing the price quote to at least one pre-selected criterion, and storing the compared price quote on a computer readable medium; and, (d) displaying the compared price quote, wherein the compared price quote comprises a price quote for a security traded in an over-the-counter financial market.

In another aspect, the invention comprises a method for generating verified price quotes for securities traded in an over-the-counter market, comprising: (a) receiving source data on a first computer readable medium, wherein the source data comprises information about the price of a security; (b) storing the source data on the computer readable medium; (c) processing the source data, wherein the processing comprises identifying suspect source data, assigning a hash key to suspect source data, wherein the hash key comprises a price quote and the identity of the data source; (d) verifying the suspect source data using the hash key, and (e) displaying information about the verified suspect source data to a user. In various embodiments, the hash key can be encrypted.

A general description of a hash function (H) is a transformation that takes a variable size input (m) and returns a fixed-size string called a hash value h, such that h=H(m). Hash functions can be one-way. A one-way hash function is selected such that it computationally infeasible to find an input x such that H(x)=h. Applications of hash functions are known to those of skill in the art, and include, for example, string hashing, cryptographic hashing, geometric hashing, and Bloom filters. Many hash functions are known to those of skill in the art.

It is known in the art that data storage and identification can be achieved through associating a data packet, or collection of data, with a key. The key and the associated data can be associated such that the key includes an address, or instructions on how to find, the data packet or collection of data associated with the key. In this context, the key and the associated data can be described as an item, wherein the item is a packet—or collection, of data or information that comprises at least a key that identifies the item—and the remainder of the data comprising the item. Hashing is a technique that has been used for calculating a storage address for a stored data item from a data item's key. Hashing has been used to convert an item's key into a random or near-random number, which is then scaled to provide the storage address for the item. The storage address is generally an address where groups of items can be stored. Generically, an item's key can be hashed to produce an identifier that can comprise a random number designating a storage address (or bin), the physical location of the storage address is ascertained (by, for example, searching a look-up table of storage addresses), and the item is then stored at the storage address (or bin). Accessing the item can be achieved by hashing the item's key to produce the identifier, ascertaining the physical location of the storage address, and searching at the storage address for the item. The key is typically expressed numerically and a random or near-random number is generated that corresponds to the key using algorithms known in the art.

Hash tables can be used to store information used to classify received packets into corresponding streams of data packets communicated (directly or indirectly) from a first node (for example, a source node) to a second node (for example, a destination node). Hash tables comprise, in general, tables of linked lists. The lists can be indexed by applying a hash function to signature information, wherein signature information comprises information that is constant with regard to corresponding data packets. Signature information can be used to relate, or correspond, data packets according to one or more suitable criteria.

A common application of hash functions is in data retrieval. In this context, data is stored on a computer readable medium such as, for example, a hard drive. The data is physically located at a storage address that corresponds to a pointer to the storage address. The pointer comprises an entry in a hash bucket, where the hash bucket can comprise multiple pointers to multiple storage addresses. The bucket is associated with a key; thus, all the pointers in the bucket are associated with the key corresponding to that particular bucket. The bucket is part of a hash table, wherein the hash table comprises a plurality of hash buckets. Each bucket has a corresponding hash key, wherein the key is generated by applying a hash function to the corresponding stored data. Data thus stored can be retrieved from the storage device by inputting a search term corresponding to the stored data, applying the hash function to the search term to obtain the hash key, locating the bucket comprising the key, identifying the pointer to the stored data associated with the search term, locating the storage address of the stored data, and comparing the stored data to the search term.

The present invention comprises novel uses of hashing in providing verified price quotes in an over-the-counter securities market.

In embodiments employing parsing of source data, parsing can include categorizing words, patterns, and/or numbers in the data source to identify market data in the source data. The parsing can be done manually—that is, by a human operator viewing the source data on a computer display, parsing, and inputting the results of the parsing into computer readable form—or the parsing can be done in whole or in part by a computer processor employing an algorithm in the form of parsing software. Suitable parsing software for identifying market data in source data includes PERL regular expressions.

The parsing can comprise parsing of quotes in any over-the-counter market of interest, including, for example, convertible, bond, index, CDS, and tranche quotes, regardless of the source or format. In various embodiments, the parser parses corporate and credit default indices. Nonlimiting examples of such indices include the Dow Jones North American Investment Grade index—or DJ CDX NA IG index, the Dow Jones North American High Yield Index—or DJ CDX NA HY index, and iTraxx indices.

In various embodiments, the invention helps users and market participants efficiently aggregate available data in real-time by parsing structured and unstructured emails and website text, and populating a database with the market quotes organized by tradable contract, market maker, and bid and offer levels. Via any suitable add-ins, such as, for example, a GUI and Excel add-in, users and market participants can see for a given contract, a bid/offer stack of prices shown to them by their counterparties. For example, at a single glance, a trader is able to see with which counterparty they can get best execution and at what level. Accordingly, traders in over-the-counter markets can see all relevant market quotes shown to them in a single screen or display, leading to faster and better execution.

In various embodiments, the at least one criterion is a criterion that identifies suspect data. Suspect data comprises data that includes market prices that are outside an expected range of values and contracts of unusually short or unusually long tenor. Designating source data as suspect data can be achieved by a human operator, having viewed the source data in computer readable form, and applying the criterion (or criteria) to the source data and deciding, based on the criterion (or criteria) whether the data is suspect or not.

Where data is not designated as suspect, the price quote can be extracted from the data and displayed to a user in, for example, a ranking of price quotes associated with the identity of the originator of the price quote. Where data is designated as suspect, the source data is further examined to determine whether it is indeed valid, or has been miscategorized (in which case it is recategorized).

In various embodiments, source data arrives at a single location, wherein the location comprises a system comprising at least one device capable of receiving the source data (such as, for example, an input device), at least one processor, and a medium for storing computer readable data. The method can be carried out at a single location.

In various embodiments, the method can be carried out at more than one location. In one nonlimiting example, the method can be carried out as follows: A first system comprising at least one input device capable of receiving the source data, at least one processor, and at least one storage medium, receives source data. The processor, according to at least one pre-selected criterion, determines which source data comprises suspect source data. Once identified, suspect source data is compiled by the source data and stored. The stored suspect source data comprises at least price information and the originator of the price information. In this context, the originator of the price information includes the address (e.g., one or more of email address, url, IP address, postal address, phone number, company name, etc.) of the entity or person where the price information appeared.

In various embodiments, the step of verifying the suspect source data using the hash key comprises transmitting the suspect source data in the hash key to a verifier, wherein the verifier verifies the suspect source data and transmits to a user a computer readable message comprising a verification, a verification failure, or a combination thereof.

The suspect source data can be stored in a secure form. The secure form can comprise, as described herein, a hash key or hash table that comprises information at least about the originator of a price quote and the price quote itself. Suspect source data from more than one source can be stored together. For example, identities of originators and the price quotes from each originator can be saved together in a single secure form for transmission over a telecommunications line.

The telecommunications line can include a secure line or an insecure line. The transmission can be achieved on an insecure line without the likelihood of revealing the identity of the originator and the price quote being revealed, because the identity of the originator and the associated price quote are encoded in a hash key or encrypted hash key or hash table as described herein. Advantages of this embodiment include the ability to compile, or mix, two or more price quotes associated with two or more originators into a single transmission. Only recipients that are able to gain access to the information in the hash key or hash table can view the identity of the originator and the associated price quote. In various embodiments, the hash key and/or hash table can be encrypted employing a suitable encryption method known in the art. Suitable encryption methods are described herein.

The invention comprises a computer-implemented system that facilitates the real time aggregation of structured and unstructured electronic market data sources for over-the-counter financial markets. This includes a method and system by which new formats of source data can be categorized and processed. Using this system, source data can be made anonymous and uniquely identifiable. The system can be built around a centralized hub, and users can submit their source data for categorization, the resultant categorized source data being returned and stored locally at a client. Or the categorized source data can be stored at a location distant from a client and accessed remotely by a client. The systems of the invention can be maintained by a central administrator, peers (i.e., users), or a combination thereof. The system can also be maintained locally.

Embodiments of the invention include methods, software, and systems that parse emails and websites for dealer quotes in certain over-the-counter derivatives. Such embodiments may include a data flow system ("Data Flow System") for the cleaning of data identified as anomalous without breaching copyrights and rights of confidentiality in the anomalous data of the creator of the relevant data (e.g., email or website). Anomalous data are identified on an exception basis and manually checked and cleaned, resulting in accurate and comprehensive output.

Advantages of the methods, software, and systems described herein include, for example, access to high quality, verified source data in real time. The methods, software, and systems can, for example, store quotes in a local database, enable traders to access and analyze stored quotes by, for example, a graphical user interface or an add-in such as, for example, a Microsoft Excel add-in; allow traders to access quotes tick-by-tick; allow traders to readily view ranked bids and offers; enable traders to determine best available prices for any given security and the identity of the relevant dealer; enable traders to perform complex analytics across a portfolio of securities; and enable traders to more accurately mark-to-market their books.

Nonlimiting examples of over-the-counter markets for which the invention is useful include the corporate bond market, the convertible bond market, the credit default swap market, the credit indexes market and the index tranches market.

The methods, software, and systems described herein can be readily adapted to a wide variety of over-the-counter markets or phenomena such as, for example, high yield bonds, convertible bonds, equity volatility, etc. One application of the invention includes a price quote system for a credit default swap (CDS) market, where a typical trader receives around 1,500 emails a day, containing over 3,000 distinct market quotes. Real time ranked bids and offers allows users to analyze the depth of the market for each security and virtually instantly survey up-to-date price histories that can be used to compare current quotes with stored price quotes. The exception-based cleaning embodiments of the invention help ensure data integrity and reliability. Anomalous data is identified on an exception basis and manually checked and cleaned, resulting in an accurate and comprehensive output. With the present invention, financial market participant such as, for example, traders, portfolio managers, and risk managers, can now enjoy a real-time price quote parsing tool that includes the structuring of market pricing data that can enhance trading performance and reduce costs.

Having been subject to comparison with one or more pre-selected criteria, the source data can be stored in a computer readable medium. Before or after storage, the compared source data can be categorized, or placed in virtual bins, according to the comparison(s). The compared source data can be displayed in any suitable or desirable format for viewing by a user. One desirable format comprises a price quote in a ranking of price quotes, wherein the originator of the price quote is identified in conjunction with the price quote. In this way, a user can readily inspect a display that comprises price quotes generated from a variety of source data, organized in a ranked display of increasing or decreasing prices for a particular security, and the identity and/or contact information for the originator of the price quote.

The method can further comprise the step of processing the source data, wherein the step comprises parsing the source data before, after, or during comparing the source data to the at least one pre-selected criterion.

In various embodiments, the source data can be received from multiple sources, and the source data can comprise more than one price quote for the security. The source data can be from multiple sources, and each the data from the multiple sources need not be in the same format. Formats can include, for example, email, html, text, xml, or combinations thereof. For example, a data comprising an email can be received from a first source, and data comprising html— or a web page or link—can be received from a second source. Both the email and the html data include a price quote for a security that is relevant in an over-the-counter market. The multiple sources can number, for example, in the thousands. Each data source can comprise more than one price quote.

The invention can be practiced in a distributed computing environment or network where processes can be carried out by processing devices that are linked through, for example, a communications network. Distributed computing environments include computer networks. Distributed computing environments include environments where computer executable instructions can be located in either or both local and remote computer storage media, including in computer readable media (CRM) such as, for example, memory storage devices. Memory storage devices include, for example, hard drives, suitable optical disks such as CD-ROMs, floppy disks, ROM (read only memory), PROM (programmable read only memory), RAM (random access memory), EPROM (erasable programmable read only memory), EEPROM (electrically erasable programmable read only memory), flash EPROM (i.e., nonvolatile memory) memory cards, flash memory, or any other suitable computer-readable media. The invention can be practiced using any suitable hardware, software, firmware, or combination thereof.

Where a process can take place by way of a computer, the process can be carried out by any suitable executable instructions. Computer executable instructions include routines, subroutines, computer programs, objects, data structures, and the like that perform certain functions or manipulate or implement data types of interest.

The invention can be practiced with any suitable combination of processing; input/output devices; display devices; and/or general-purpose or special-purpose processors or logic circuits programmed with the methods of the invention. Such devices can include, for example, personal computers, servers, client devices, personal data assistants (PDAs), hand-held devices, laptops, programmable electronics, computer networks such as, for example, a personal computer (PCT) network, a mainframe, a miniframe, and a suitable distributed computing environments that includes any of the foregoing.

The computer readable medium can comprise any suitable computer readable medium known in the art. For example, the computer readable medium can comprise a mainframe or desktop computer, wherein the mainframe or desktop comprises an input enabling the computer to receive the data sources. The mainframe or desktop further comprises software capable of receiving and storing the data sources.

Suitable software capable of receiving and storing the data sources include MICROSOFT™ Exchange Server and MICROSOFT SQL server.

The source data in computer readable form is processed using a computer processor. Suitable computer processors include INTEL® PENTIUM® 4 2.80 GHz. Employing the suitable processor, a price quote is extracted from the source data. The extracting can be done manually, that is, by a human operator, or can be achieved employing a computer program to identify and extract price data from the source data. A suitable computer program to identify and extract price data from the source data includes PERL regular expressions. Once the price data is extracted, it can be stored and/or directly used to compare the price data to at least one pre-selected criterion. The pre-selected criterion can include, for example, most recent asset price bid and offer.

One feature of the invention is scalability, wherein the scalability stems from the observation that in a given market, there are actually a very small number of participants generating original email markets. Within a typical investment bank, there will normally only be one trader making a market on a given asset. This information is communicated by email to a sales team who then, having perhaps added their own market commentary, forward the markets to their clients.

This market data flow is depicted in FIG. 1. This commonality gives rise to two important results: (1) the markets made by the original trader are received in the same format by most, if not all clients; and, (2) any systematic error, or bad data produced during the parsing process, is the same for all recipients, and by grouping suspect data together, is inspected or edited only once.

Figure 2:
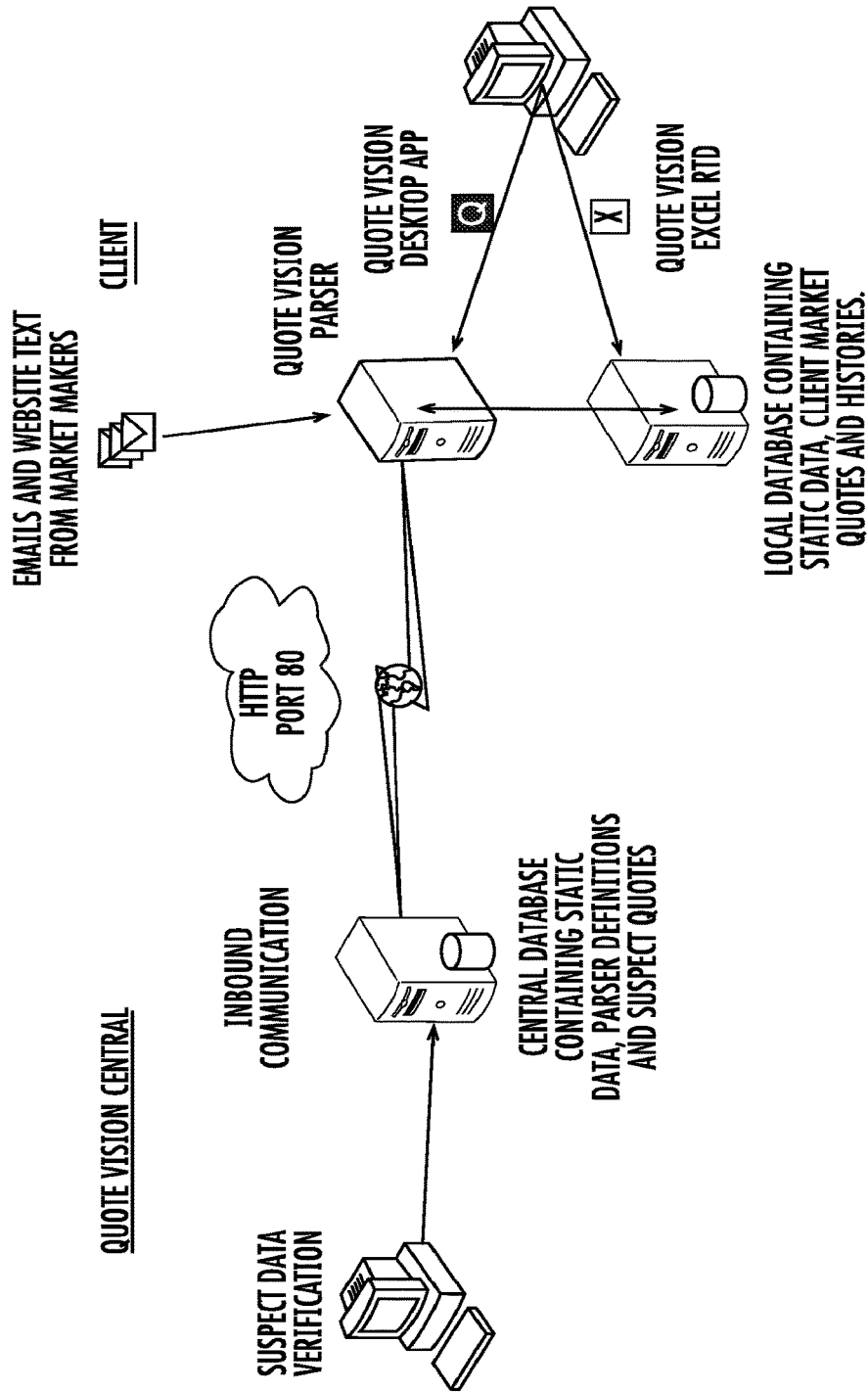
FIG. 2 illustrates an embodiment of the invention comprising a client architecture for handling source data.

In one embodiment, the invention comprises four main components. A nonlimiting example of the arrangement of the components is depicted in FIG. 2. The first component is the parser which categorizes words, patterns and numbers in the incoming email or website text, and at present uses an expert system to capture the market data contained therein. Other methods considered for the parser engine include neural networks, a template based system (for structured text), Bayesian networks, natural language processing, and layered combinations of the previous methods for increased yields from markets including both structured and unstructured source formats The components for all configurations can be the same, or similar. Differing configurations can be employed to select the most suitable layout given prevailing solution scalability.

Once the text has been parsed, the captured market quotes are compared with an expectation level for the given asset, and if within range, are added to the database and visible output as "clean" quotes. Quotes falling outside the expected range are flagged for manual verification. These are either a result of valid large market movements or parser misclassification.

Financial markets are always rapidly evolving both in terms of asset types, entities on which the assets are traded and the quoting conventions and formats used. In order to keep abreast of these changes, static data needs to be continuously enhanced and parser definitions need to be updated. For each user to do this independently makes little sense due to the duplication of effort involved and specialist knowledge and skill set required. To satisfy these needs, the invention can comprise incorporation of a centralized service that updates client installations with up to date static data and parser definitions on a daily basis.

In order to satisfy legal requirements for the forwarding of suspect quotes to an external third party for verification, the source of the quotes has to be anonymous. However, in order to pool suspect quotes for verification, the source has to be included. The solution the invention implements is to create a hash key from a combination of the basic quote information (bid, offer, entity, term, etc.) and source. This hash key can then be encrypted using the MD5 algorithm to create a unique, anonymous identifier. Suspect quotes then received centrally with the same hash key are grouped and processed together as one quote.

In a similar fashion the associated body text of the source email or website can be sent in its entirety along with a suspect quote to aid the data verification process. In this instance, the parser stores down the column and row coordinates of each match it makes that is not in itself an actual quote level. These coordinates are rebased to the first match to account for any offsets, and combined with the actual match text to generate a format hash key.

By including the rebased coordinates in a quote sent for inspection along with the format hash key, any systematic misparsing requiring recategorization or editing of the quote during validation can be automate after the first intervention by applying the changes made to all future instances.

Figure 3:
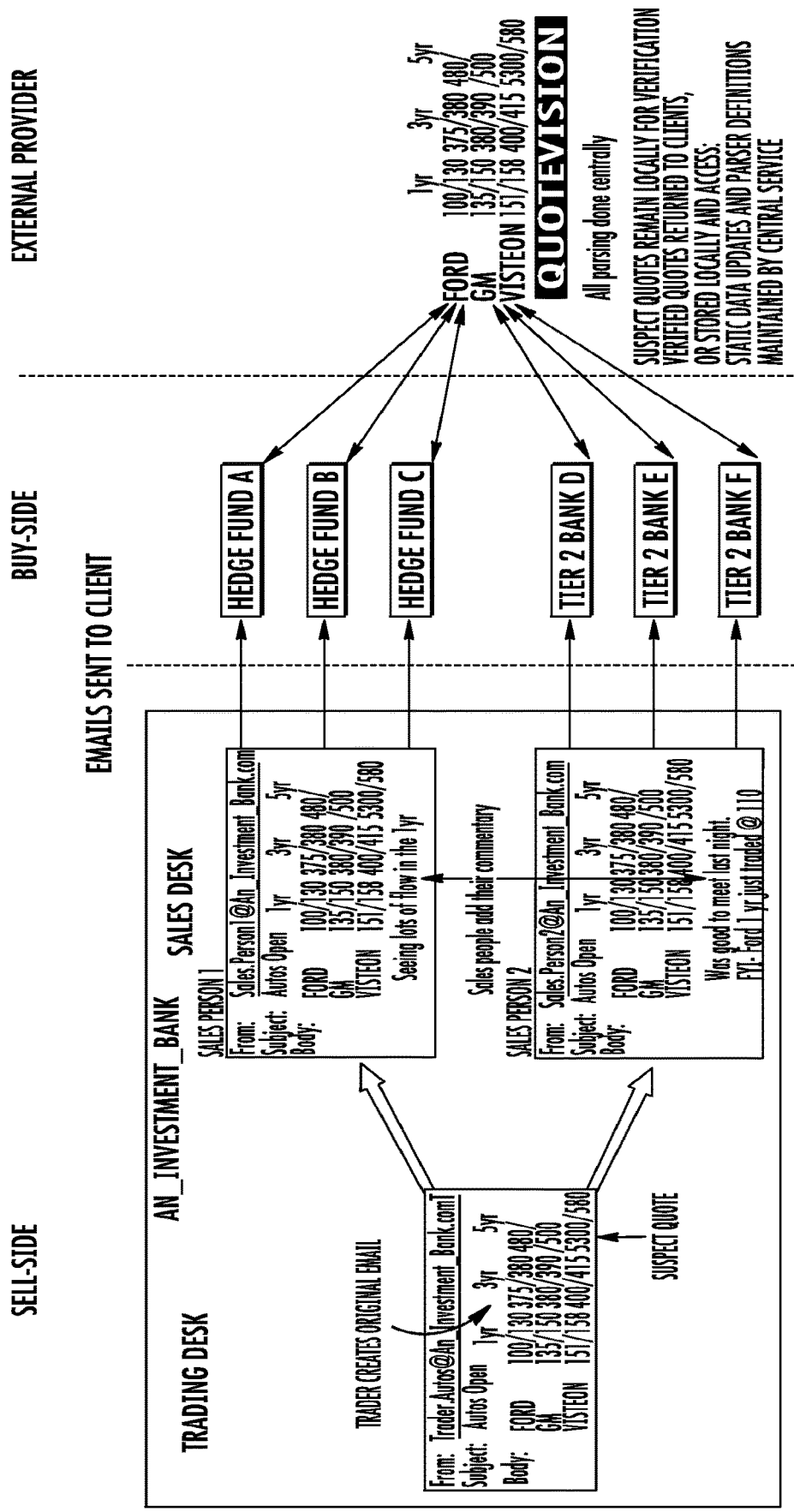
FIG. 3 illustrates an embodiment of the invention comprising employing a single central parser processing data from a number of clients.

These restrictions of confidentiality do not apply to all participants in the market. For example, hedge funds that outsource their middle and back office functions (risk management) could reasonably be expected to forward any markets they are shown to their risk managers to verify that the books are being marked correctly. In this scenario, the system could be configured slightly differently, with one central parser, processing data from a number of clients as in FIG. 3.

Figure 5:
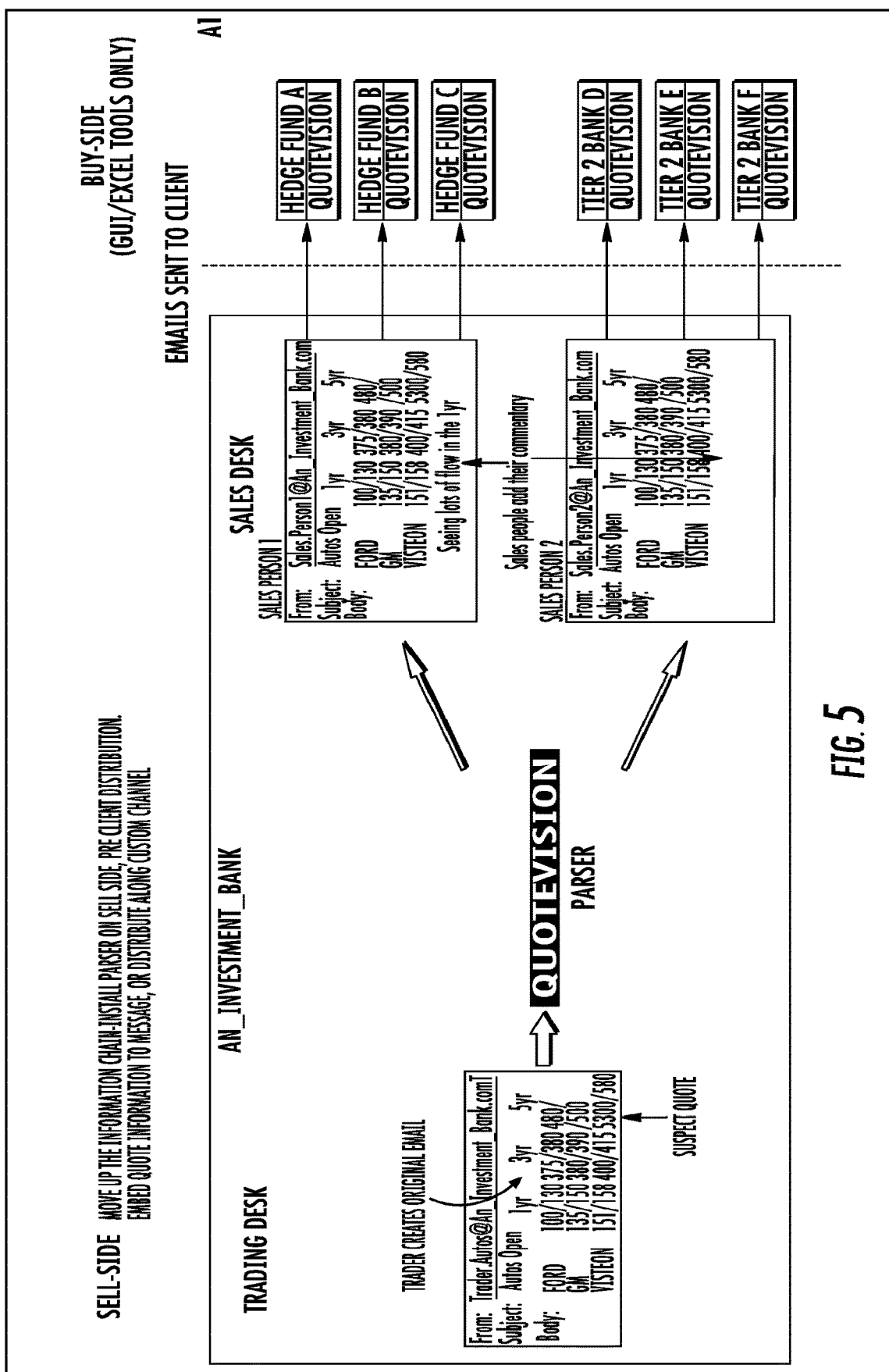
FIG. 5 illustrates an embodiment of the invention comprising employing a system employed by originators of market data, wherein the system is employed to either preformat email or use email to create quotes for distribution to clients.

In another embodiment, originators of the market data employ the methods, software, and/or hardware of the invention to either preformat email, or to create quotes for distribution to clients as in FIG. 5.

Figure 6:
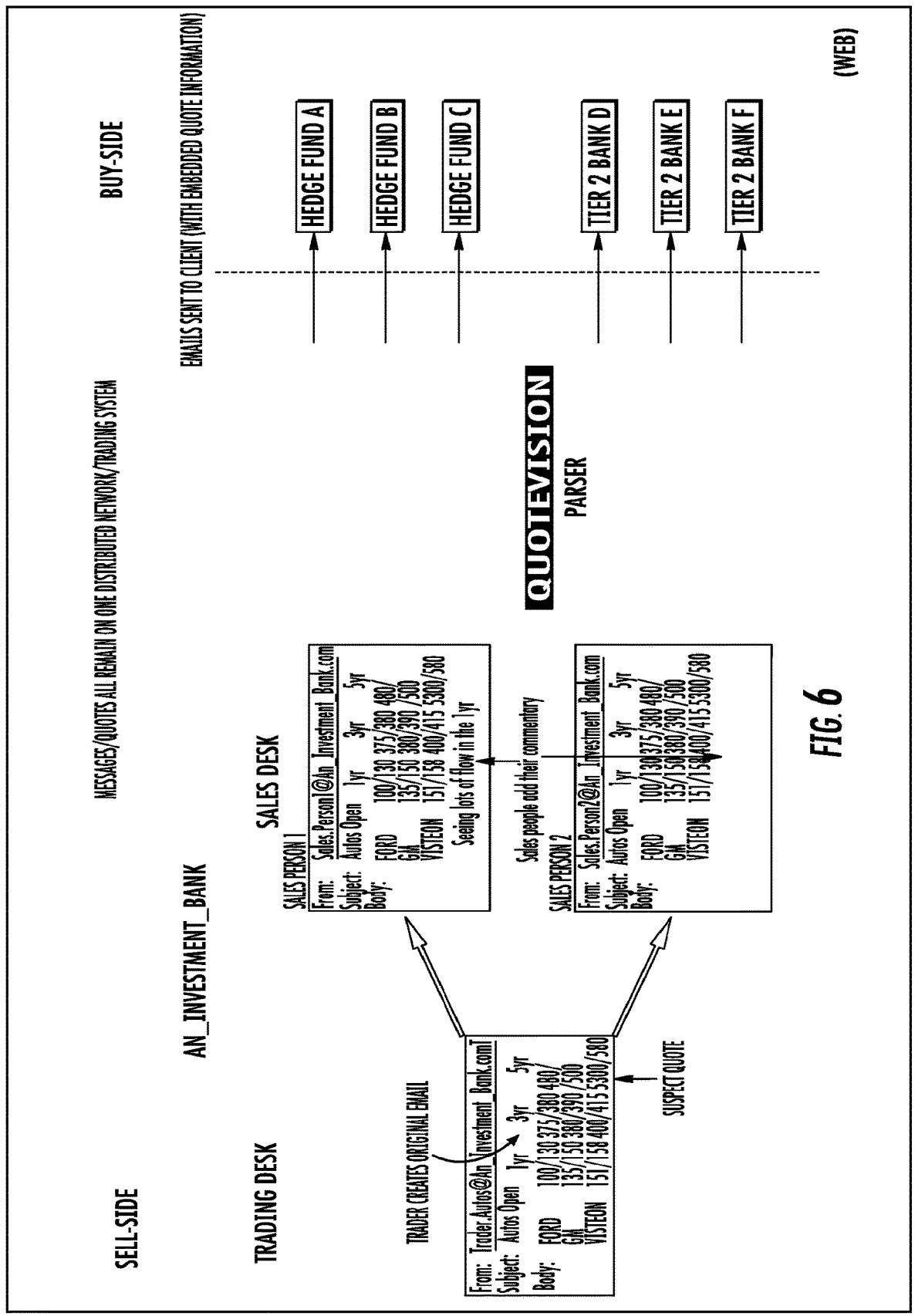
FIG. 6 illustrates an embodiment of the invention comprising a parser located within a common communication/messaging network such that quotes are distributed with, or instead of, original text from source data.

In another embodiment, a parser is located within a common communication/messaging network, such that quotes are distributed along with—or instead of—the original text from which they were derived as in FIG. 6.

Figure 4:
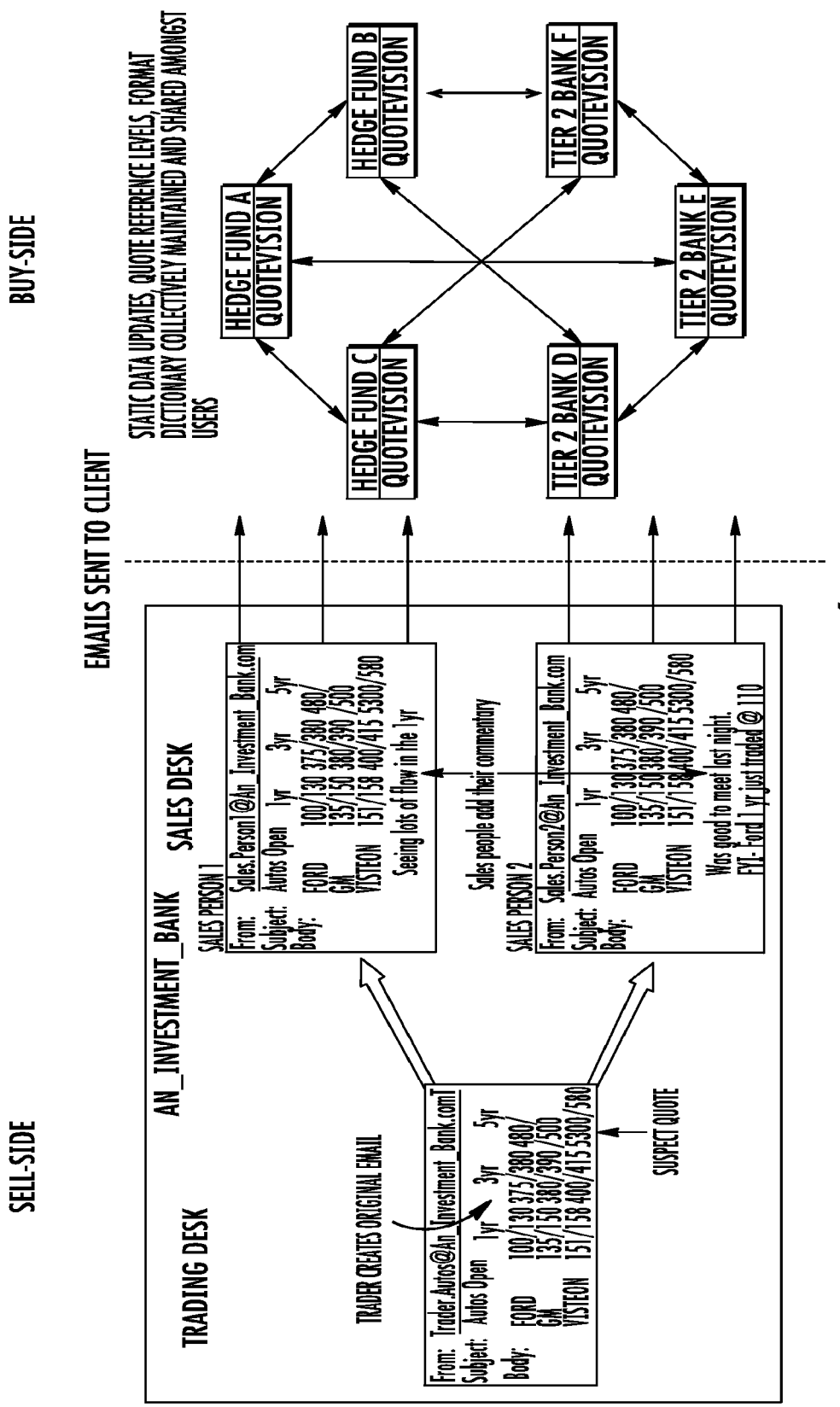
FIG. 4 illustrates an embodiment of the invention wherein each user shares system maintenance, and updates are shared between peers.

In another embodiment, a system is configured so that each user shares the maintenance of the system, with updates being shared between peers as in FIG. 4.

Figure 7:
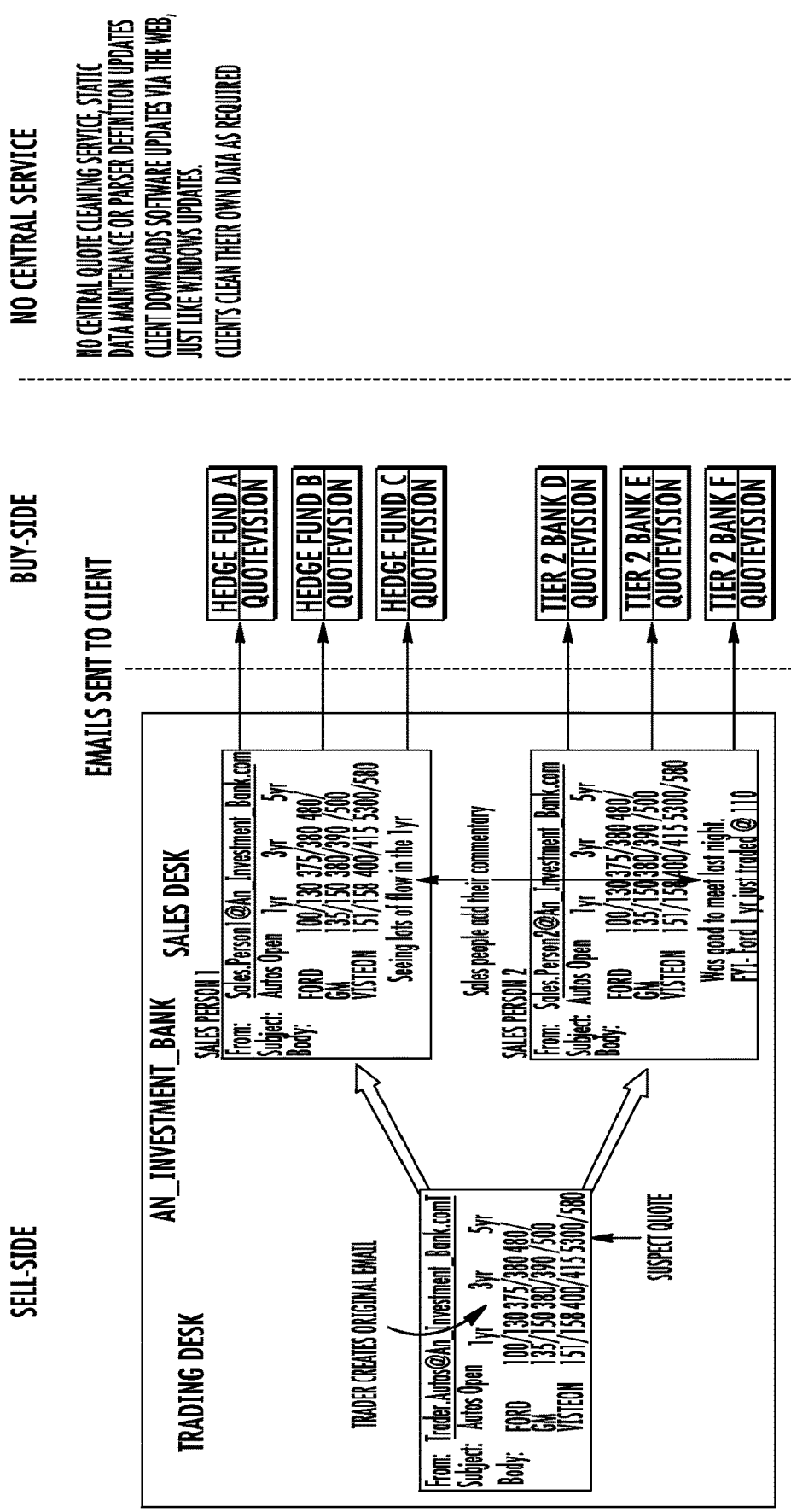
FIG. 7 illustrates an embodiment of the invention for markets where no central maintenance and verification are needed, and is maintained instead by clients and through periodic software updates.

In another embodiment, for markets with well structured/consistent data sources, no central maintenance and verification may be desired. In this configuration (illustrated by example in FIG. 7), the system could be maintained by clients, and through periodic software updates.

Figure 8:
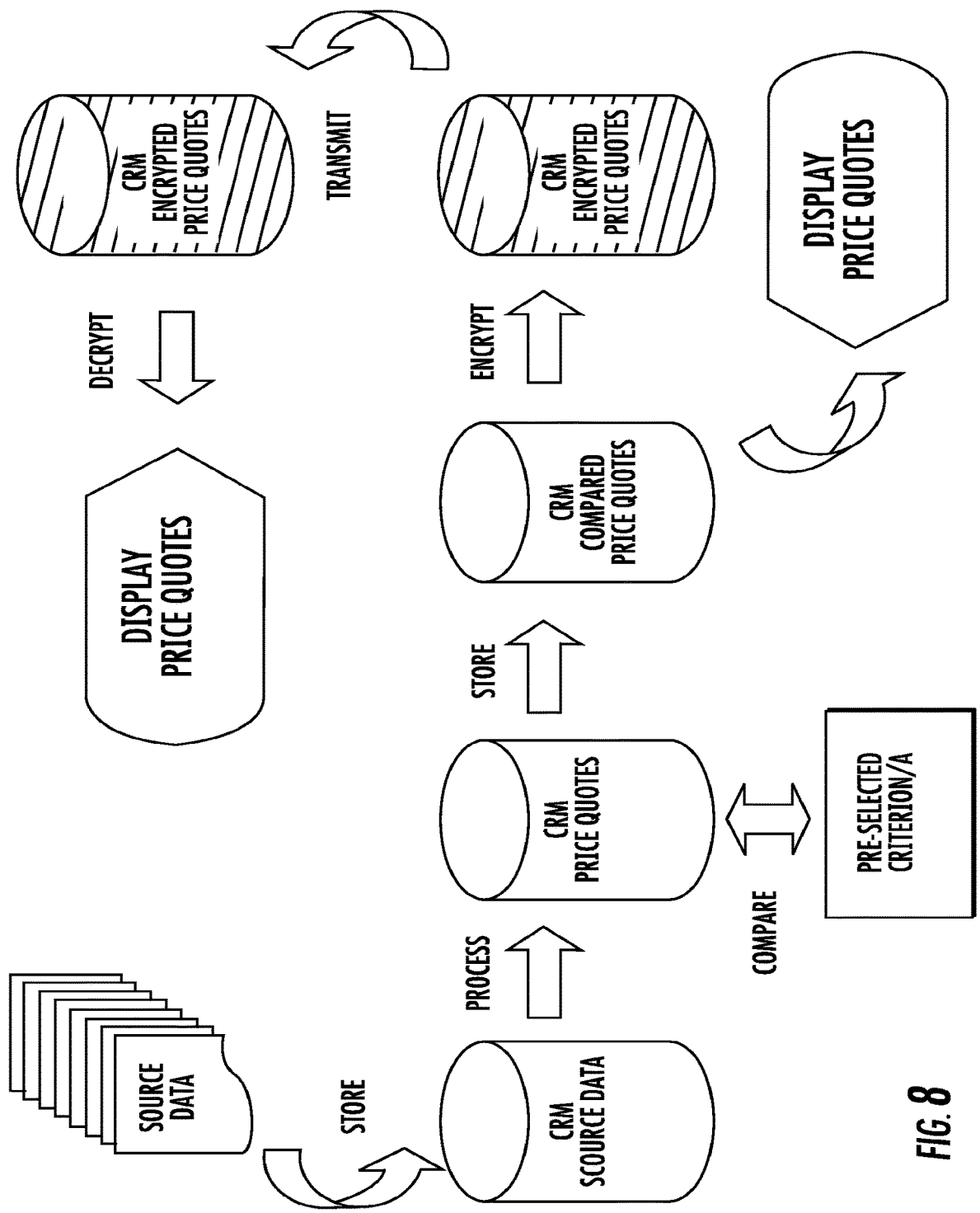
FIG. 8 illustrates a process of the invention wherein source data, which can comprise data in any format, is stored on a computer readable medium (CRM), processed by, for example, parsing, then stored again, and compared to at least one pre-selected criterion.

FIG. 8 illustrates a process of the invention wherein source data, which can comprise data in any format, is stored on a computer readable medium (CRM), processed by, for example, parsing, then stored again, and compared to at least one pre-selected criterion.

Figure 9:
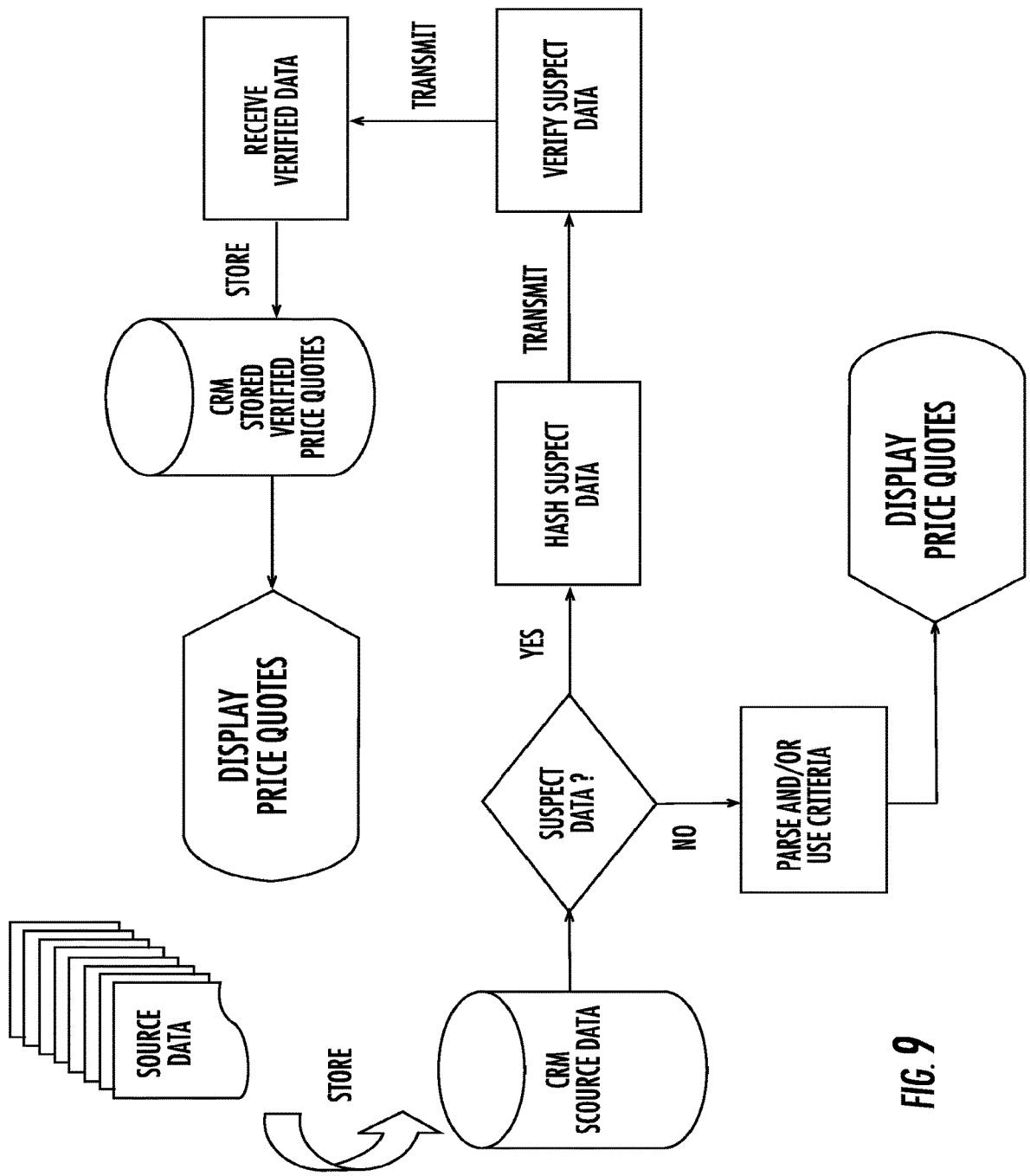
FIG. 9 illustrates one embodiment wherein verification is achieved through transmission of hashed suspect source data.

FIG. 9 illustrates a similar process, but with identification and verification of suspect data. In the embodiment shown, verification is achieved through transmission of hashed suspect source data. In other embodiments, such as, for example, where the methods, software, and hardware of the invention are practiced on a local network, transmission may not be necessary. Although not shown, the transmitted data can be encrypted. Following display of price quotes or verified price quotes, the user preferably selects the best price for an over-the-counter security and places an order to the originator of the best price.

Figure 10:
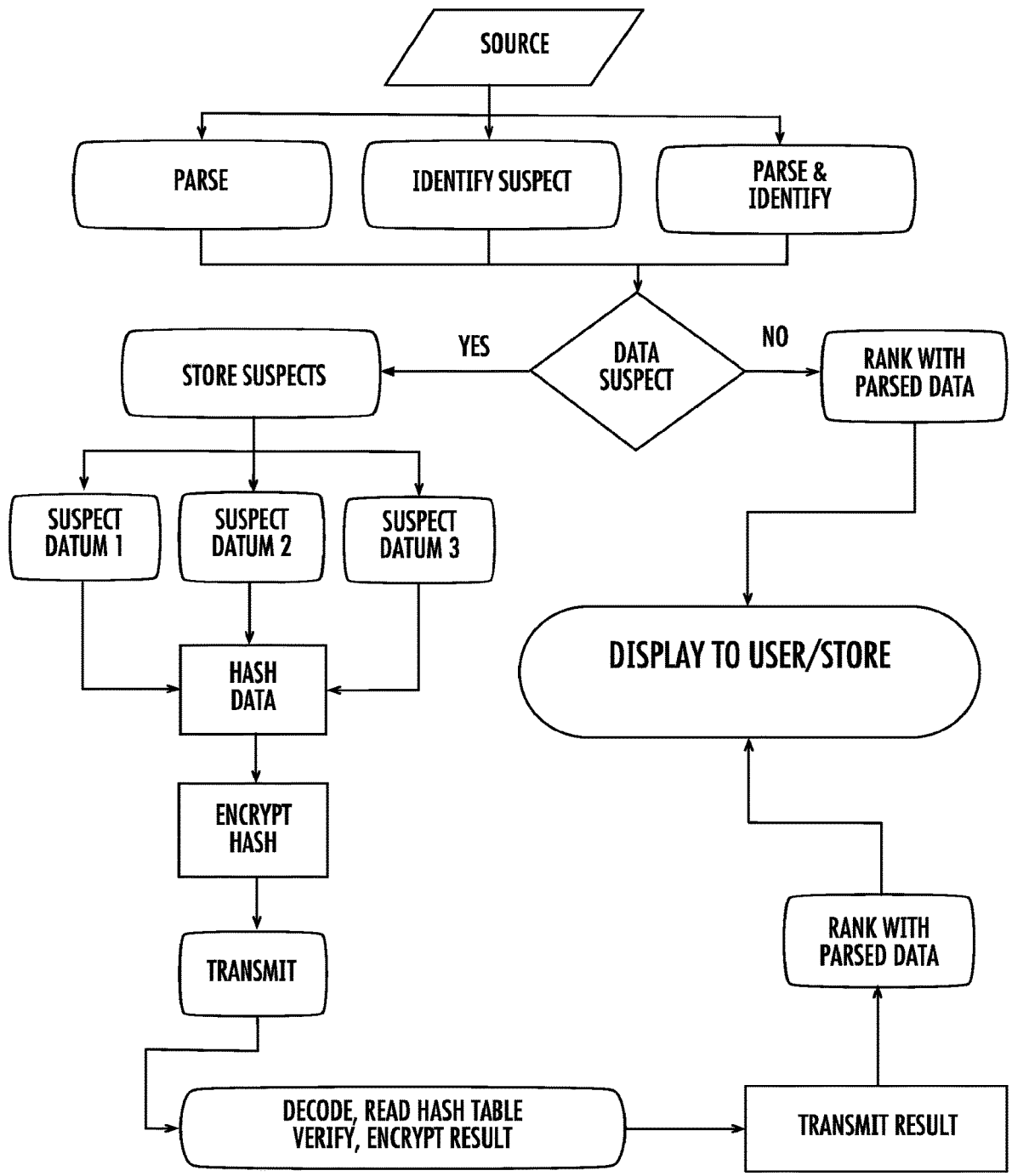
FIG. 10 illustrates one embodiment of the invention that shows how hashing can be used in at least one embodiment in generating verified price quotes on an over-the-counter security.

FIG. 10 illustrates a process of the invention that shows how hashing can be used in at least one embodiment in generating verified price quotes. In the embodiment illustrated, suspect data is hashed, and a resulting hash key is encrypted. In general, however, encryption of the hash key is not required. Following display of price quotes or verified price quotes, the user preferably selects the best price for an over-the-counter security and places an order to the originator of the best price. At any suitable step in the process, data can be stored on a computer readable medium.

Figure 11:
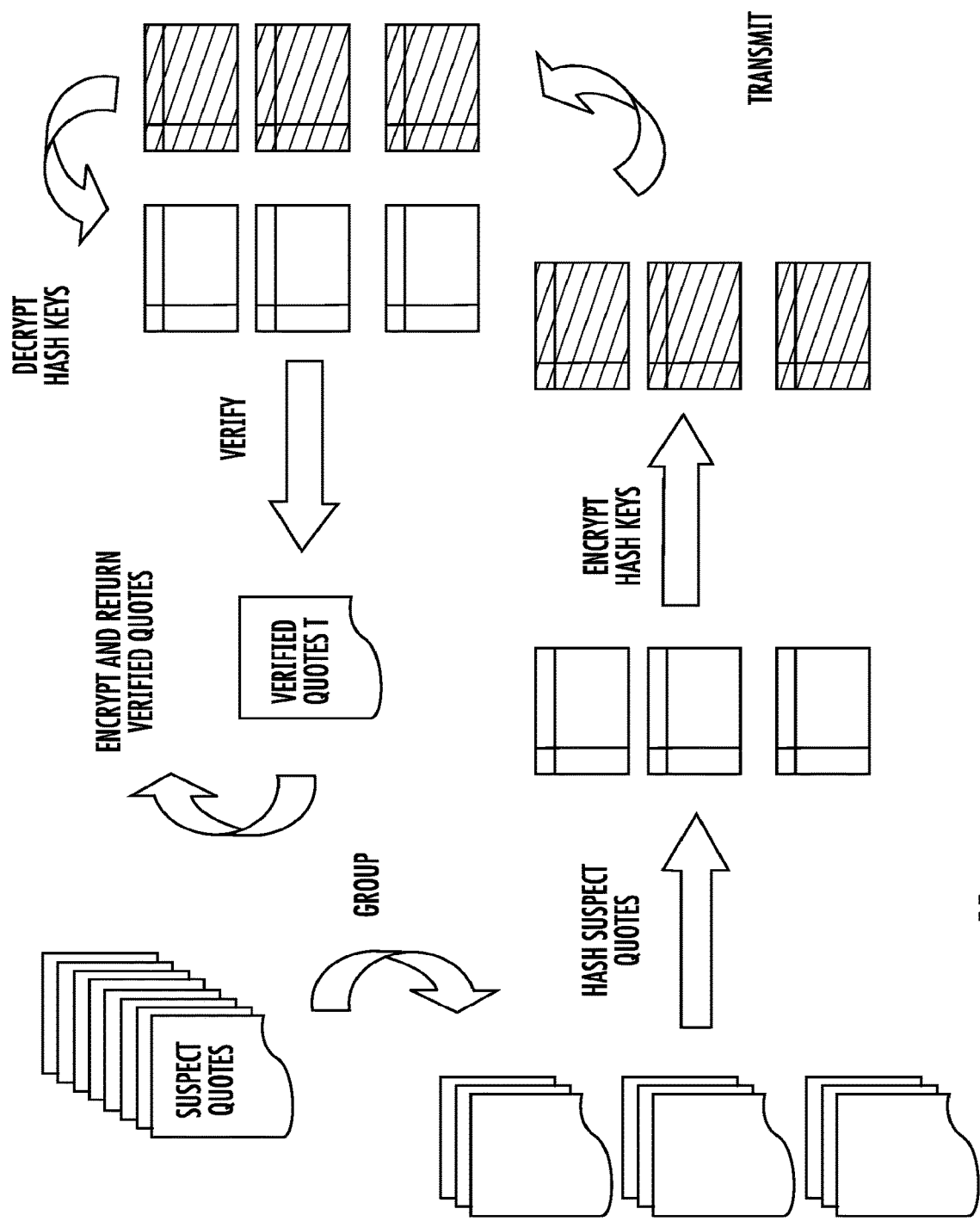
FIG. 11 illustrates one embodiment using an encrypted hash key to generate verified price quotes on an over-the-counter security.

FIG. 11 illustrates an embodiment where data comprising suspect quotes for an over-the-counter security are hashed, the hash keys are encrypted, transmitted to, for example, a remote hub or location, the hash keys decrypted and the quotes verified, the verified quotes re-hashed and transmitted back, and then the hash keys decrypted and verified price quotes extracted. Storage onto a computer readable medium, and display of the data, is not indicated in the process diagram. However, the suspect quotes, hashed data, encrypted keys, and the like can be conveniently stored on a suitable computer readable medium at any convenient step in the process. The verified quotes are preferably displayed to a user on a display such as a computer terminal, and preferably ranked according to price. The user can then select the best price and place an order according to the displayed verified price quotes.

Advantages of the invention include the ability to determine best market prices in real time and track price histories for over-the-counter securities, thus enabling users to price portfolios using verified market prices in real time. The invention also provides the ability to store verified price data and manipulate it in any suitable manner such as, for example, commercial spreadsheet applications.

The capability of pricing a portfolio in real time with verified price quote data provides a significant advantage to users, and in particular to risk managers. Because the invention provides verified price quote data in over-the-counter markets, the invention allows users to apply more accurate data to mathematical models of risk assessment. Accordingly, users can better manage portfolios by improved estimation of market risks in over-the-counter markets. A nonlimiting example of a mathematical approach to risk assessment that can benefit from the invention includes statistical measures of risk exposure that generate probabilistic statements. For example, users can use the invention to improve the process of determining Value-at-Risk (VaR) by providing not only accurate historical price data, but verified real time price quotes that can be used to provide an accurate, verified current portfolio position.

Accordingly, the invention also comprises a method for computing VaR, comprising employing the methods of the invention to generate real time price quotes, including verified price quotes, and using the real time price quotes in a VaR method. Any suitable VaR model or algorithm can be used in connection with the invention. In some embodiments, the invention comprises employing the methods of the invention to generate verified price quotes and using the verified price quotes to compute a VaR for a portfolio, wherein the VaR is employed to set trading limits on the securities comprising the portfolio.

EXAMPLES

The following examples are intended to explain the invention further.

Reducing Misclassifications

The idea behind the use of a format hash key within the invention is to significantly reduce the amount of recurring misclassifications by the parser. By creating a unique format identifier, and storing down any reclassification that has to be done by the data editing team, it is possible to prevent or at least automate the handling of further occurrences.

An algorithm creates a hash key from all matches made by the parser, with the exception of any relating to the actual level of quotes, as these will always be changing. By creating a hash key using these actual matches, and their rebased coordinates within the text, it is possible to uniquely identify formats. In one embodiment, the rebase of coordinates is done onto the first included match.

Consider the example emails below. Both generate the same hash key, and when combined with the rebased coordinate of the actual quote match uniquely identify the instance of a quote. TABLE-US-00001 RHODIA CURVE UPDATE—5 bps wider today (results in line+general softer market tone as evidence by equity) 1 y 160/210 2y 365/415 3y 455/465 5y 515/530 7y 535/555 10y 555/580 5 m.times.5 m RHODIA CURVE 1y 155/205 2y 360/410 3y 450/460 5y 510/525 7y 530/550 10y 550/

Hash Key:

RHODIA(0,0)1Y(1,2)2Y(1,3)3 Y(1,4)5 Y(1,5)7Y(1,6) 10Y(0,7)

Encrypted Hash Key:

2zi+EFLV9kx/t/+o8S/i+g==

Using Hash Keys in the Credit Default SwapMarket

In one example of a CDS application of the invention, the HashKey will identify a CDS quote and have the qualities of uniqueness and encryption as described below. Here, the HashKey is especially not intended as a compressed-data mechanism for decryption at a central hub, further described below.

HashKey Uniqueness

A CDS quote scraped by a suitable parser comprises two sets of properties, those relating to the underlying email and those relating to the quote itself. Properties of the underlying email are not conducive to identifying quote uniqueness. If a trader were to send the same quote within multiple emails a short time apart, the inclusion of email specific properties within the HashKey would invalidate the quotes' uniqueness. TABLE-US-00002 EMAIL PROPERTY REASON FOR NOT INCLUDING IN HASHKEY emailId Not unique per client. recFrom Resolves to a traders Bloomberg a/c—not the email originator. sentTo Different client recipients. sent Differing forward timestamps from each Bloomberg mailbox. body Contains non-unique embedded forwardinfo.

TABLE-US-00003 Client database Emails table. Properties of a scraped CDS quote are by definition ideal for defining uniqueness. CDS QUOTE INCLUDE IN PROPERTY HASHKEY COMMENT quoteId No Not unique per client. entityId Yes bid Yes offer Yes upfBid Yes upf=upfront. upfOffer Yes upf=upfront. isTradedQuote No Very rarely differs between quotes. term Yes termDate Yes dealTypeId Yes currencyId Yes bidSize No Very rarely differs between quotes. offerSize No Very rarely differs between quotes. sourceId Yes See .sup.1 below. quoteDate Yes quoteTime Yes See .sup.2 below. emailId No Not unique per client. active No Status changes during a quotes lifetime. UserId No Not unique per client. LastAction No Not unique per client.

TABLE-US-00004 Client database CdsQuotes table. CDS QUOTE INCLUDE IN PROPERTY HASHKEY COMMENT contextStart No First character of the quotes' context within the Emails table body field. See .sup.3 below. contextFinish No Last character of the quotes' context within the Emails table body field. See .sup.3 below. hashKey No .sup.1 The sourceId contributes a sizeable weight to a CDS quotes' uniqueness, therefore, it is preferable to include. RS confirms that provided the HashKey is not decrypted at hashkey does not get decrypted # anywhere. Is it purely used to identify uniqueness anonymously. or FDE Central then it is fine to use. .sup.2 In this example, the quoteTime is imperative for Data Editing purposes. It is the receipt time of the underlying email. A variation of only 1 second will invalidate a quotes' uniqueness. Therefore, for inclusion in the HashKey the quote time will be floored to three 20-minute # segments per hour. For example, quotes arriving between 10:00 AM and 10:19 AM will all be timed as 10:00 AM, those arriving between 10:20 AM and 10:39 AM as 10:20 AM, etc. An exercise will be undertaken to determine the optimum number of time intervals per day or hour. A SQL join between the Emails # and CdsQuotes tables will return the actual context for the quote, to be included in the HashKey.

HashKey Encryption

Once constructed the HashKey needs to be both encrypted and obfuscated. MD5 encryption is applied to the aggregated HashKey. The result is cast to a C# string/SQL char(16) (128 bits=16 bytes) for developer convenience (TBC). MD5 was developed by Professor Ronald L. Rivest of MIT. What it does, to quote the executive summary of rfc 1321, is: The MD5 algorithm takes as input a message of arbitrary length and produces as output a 128-bit "fingerprint" or "message digest" of the input. It is conjectured that it is computationally infeasible to produce two messages having the same message digest, or to produce any message having a given pre-specified target message digest. The MD5 algorithm is intended for digital signature applications, where a large file must be "compressed" in a secure manner before being encrypted.

HashKey Algorithm

HashKey=sourceId+entityId+bid+offer+upBid+upfOffer+term+termDate+-dealTypeId+currencyId+quoteDate+quoteTime+context Verified/Reclassified data is returned to clients with the same identifying hashkey.

While the invention has been described in connection with specific embodiments thereof, it will be understood that it is capable of further modifications and this application is intended to cover any variations, uses, or adaptations of the invention following, in general, the principles of the invention and including such departure from the present disclosure as come within known or customary practice within the art to which the invention pertains and as may be applied to the essential features hereinbefore set forth and as follows in the scope of the appended claims.

We claim:

1. A method for providing real time verification and display of data identified as suspect data in an electronic trading system, the electronic trading system comprising a processor, a computer-readable medium, a screen, and a telecommunications line, the method comprising:

receiving, by the electronic trading system over the telecommunications line from multiple sources, source data comprising price data and data identifying an originator of the price data ("originator data"), the source data having multiple data formats;

identifying a portion of the source data that comprises suspect data by:

extracting one or more price quotes that include bids and offers from the source data, comparing the price quotes to at least one pre-selected criterion, and identifying as suspect data those price quotes that violate the at least one pre-selected criterion, the suspect data comprising price data and originator data from at least two different sources of the multiple sources;

verifying a validity of the suspect data in real-time by:

analyzing real-time market data, and confirming, based on the analyzing, that the suspect data from at least one of the at least two different sources of the multiple sources falls within a predetermined range of the real-time market data ("verified data"); and displaying in real time on the screen of the electronic trading system the verified data together with a portion of the source data that does not comprise the suspect data.

2. A method according to claim 1, wherein the source data is received from at least a first source and a second source, wherein the source data received from the first source is in a different format than the source data received from the second source.

3. A method according to claim 1, wherein the format of the source data comprises an email, html, text, xml, or combination thereof.

4. A method according to claim 1, wherein the step of processing the source data comprises parsing the source data before comparing the source data to the at least one pre-selected criterion.

5. A method according to claim 4, wherein the parsing comprises categorizing words, patterns, and/or numbers in the data source to identify market data in the source data.

6. A method according to claim 1, further comprising designating source data that does not meet the at least one criterion as suspect data.

7. A method according to claim 1, wherein the step of processing the source data comprises assigning an anonymous identifier to the source data.

8. The method according to claim 1, wherein analyzing real-time market data, further comprises:

compiling, together, the suspect data from said at least two different sources of the multiple sources, encoding the compiled suspect data into a single transmission using the hash key, and securely transmitting the single transmission to a third-party verification system for verification.

9. The method according to claim 8, wherein confirming, based on the analyzing, that the suspect data from at least one of the at least two different sources of the multiple sources falls within the predetermined range of the real-time market data ("verified data") comprises:

receiving results of the verification from the third party verification system, the results comprising at least one verification that the suspect data from at least one of the at least two different sources is valid.

10. The method according to claim 9, wherein the results further comprise an indication that the suspect data from at least one other of the at least two different sources in invalid.

11. The method according to claim 10, further comprising:

omitting the invalid suspect data from the screen of the electronic trading system.

12. A tangible computer-readable medium of an electronic trading system, the electronic trading system comprising the computer-readable medium, a processor, a screen, and a telecommunications line, the tangible computer-readable medium containing computer-executable instructions that when executed cause the electronic trading system to perform the steps comprising:

receiving, by the electronic trading system over the telecommunications line from multiple sources, source data comprising price data and data identifying an originator of the price data ("originator data"), the source data having multiple data formats;

identifying a portion of the source data that comprises suspect data by:

extracting one or more price quotes that include bids and offers from the source data, comparing the price quotes to at least one pre-selected criterion, and identifying as suspect data those price quotes that violate the at least one pre-selected criterion, the suspect data comprising price data and originator data from at least two different sources of the multiple sources;

verifying a validity of the suspect data in real-time by:

analyzing real-time market data, and confirming, based on the analyzing, that the suspect data from at least one of the at least two different sources of the multiple sources falls within a predetermined range of the real-time market data ("verified data"); and displaying in real time on the screen of the electronic trading system the verified data together with a portion of the source data that does not comprise the suspect data.

13. The tangible computer-readable medium of claim 12, wherein the source data received from at least a first source and a second source, wherein the source data received from the first source is in a different format than the source data received from the second source.

14. The tangible computer-readable medium of claim 12, wherein the format of the source data comprises an email, html, text, xml, or combinations thereof.

15. The tangible computer-readable medium of claim 12, wherein the step of processing the source data comprises parsing the source data before comparing the source data to the at least one pre-selected criterion.

16. The tangible computer-readable medium of claim 15, wherein the parsing comprises categorizing words, patterns, and/or numbers in the data source to identify market data in the source data.

17. The tangible computer-readable medium of claim 12, further comprising computer-executable instructions for designating source data that does not meet the at least one criterion as suspect data.

18. An electronic trading system comprising: a processor, a screen, a telecommunications line, and a tangible computer-readable medium containing computer-executable instructions that when executed cause the electronic trading system to perform the steps comprising:

receiving, by the electronic trading system over the telecommunications line from multiple sources, source data comprising price data and data identifying an originator of the price data ("originator data"), the source data having multiple data formats;

identifying a portion of the source data that comprises suspect data by:

extracting one or more price quotes that include bids and offers from the source data, comparing the price quotes to at least one pre-selected criterion, and identifying as suspect data those price quotes that violate the at least one pre-selected criterion, the suspect data comprising price data and originator data from at least two different sources of the multiple sources;

verifying a validity of the suspect data in real-time by:

analyzing real-time market data, and confirming, based on the analyzing, that the suspect data from at least one of the at least two different sources of the multiple sources falls within a predetermined range of the real-time market data ("verified data"); and displaying in real time on the screen of the electronic trading system the verified data together with a portion of the source data that does not comprise the suspect data.

19. The trading system of claim 18 wherein the source data received from at least a first source and a second source, wherein the source data received from the first source is in a different format than the source data received from the second source.

20. The trading system of claim 18, wherein the format of the source data comprises an email, html, text, xml, or combination thereof.

21. The trading system of the claim 18, wherein the step of processing the source data comprises parsing the source data before comparing the source data to the at least one pre-selected criterion.

22. The trading system of claim 21, wherein the parsing comprises categorizing words, patterns, and/or numbers in the data source to identify market data in the source data.

* * * * *